United States Patent
Kuo

(10) Patent No.: US 11,684,649 B2
(45) Date of Patent: Jun. 27, 2023

(54) USE OF MAGNOLIA FIGO EXTRACT IN THE MANUFACTURE OF COMPOUND FOR REDUCING EPIDERMAL DESQUAMATION AND PROMOTING WOUND HEALING

(71) Applicants: FETHIANN MOLECULE APPLIED CO., LTD., Yilan (TW); Chun-Sheng Kuo, Taichung (TW)

(72) Inventor: Chun-Sheng Kuo, Taichung (TW)

(73) Assignees: FETHIANN MOLECULE APPLIED CO., LTD., Yilan (TW); Chun-Sheng Kuo, Taichung (TW)

( * ) Notice: Subject to any disclaimer, the term of this patent is extended or adjusted under 35 U.S.C. 154(b) by 227 days.

(21) Appl. No.: 17/149,642

(22) Filed: Jan. 14, 2021

(65) Prior Publication Data

US 2022/0152141 A1 May 19, 2022

(30) Foreign Application Priority Data

Nov. 17, 2020 (TW) .................................. 109140018

(51) Int. Cl.
*A61K 36/00* (2006.01)
*A61K 36/575* (2006.01)
*A61K 8/9789* (2017.01)
*A61K 8/92* (2006.01)
*A61Q 19/00* (2006.01)

(52) U.S. Cl.
CPC ............ *A61K 36/575* (2013.01); *A61K 8/922* (2013.01); *A61K 8/9789* (2017.08); *A61Q 19/00* (2013.01)

(58) Field of Classification Search
CPC ....................................................... A61P 17/02
See application file for complete search history.

(56) References Cited

U.S. PATENT DOCUMENTS

2013/0330426 A1* 12/2013 Florence ................ A61K 8/062
424/725

FOREIGN PATENT DOCUMENTS

| CN | 107854577 A | * | 3/2018 |
| KR | 20190019624 A | * | 2/2019 |

* cited by examiner

*Primary Examiner* — Qiuwen Mi

(57) ABSTRACT

A use of *Magnolia figo* extract in the manufacture of a compound for reducing epidermal desquamation and promoting wound healing.

5 Claims, 8 Drawing Sheets

USE OF MAGNOLIA FIGO EXTRACT IN THE MANUFACTURE OF COMPOUND FOR REDUCING EPIDERMAL DESQUAMATION AND PROMOTING WOUND HEALING

FIELD OF THE INVENTION

The present invention relates to a use of *Magnolia figo* extract, and particularly relates to a use of *Magnolia figo* extract in the manufacture of a compound for reducing epidermal desquamation and promoting wound healing.

BACKGROUND OF THE INVENTION

Human skin fibroblast and blood vessels around it become losing flexibility due to many factors such as aging, environment, food or sleep. At the same time, the collagen, which is originally rich in the skin, also gradually be lost, which cause poor skin condition. Therefore many biomedical materials and skin medical related products have been developing to relieve and improve skin conditions.

Most known biomedical materials and skin medical related products contain animal-derived ingredients. The animal-derived ingredients usually have larger molecular weight and belong to macromolecular, causing problems of barely absorbed by skin or only absorbed by skin surface but unable to reach the deep layer of the skin. Thus, it is difficult to fundamentally improve or solve the skin problem. Furthermore, biomedical materials and skin medical related products made by animal-derived ingredients exist potentially controversy on moral level.

The histological structure of human skin can be divided into epidermis, dermis, and subcutis or subcutaneous tissue. In general, the epidermis can be divided into four to five layers, including, from top to bottom, stratum corneum (without viable cells), stratum lucidum, stratum granulosum, stratum spinosum and stratum basale.

Stratum corneum is formed by non-viable corneocytes. The corneocytes continue multiplying, migrating outward, and lifting up until reaching the outermost surface of epidermis. Old stratum corneum at the outermost surface will shed as dander to maintain the stratum corneum in a certain thickness. The frequent replacement from stratum basale to stratum corneum is called skin renewal. Speed of skin renewal varies with personal physique, body part, and age. In general, the period from forming stratum basale to stratum corneum is about two weeks, also known as "a small cycle of skin growth", and the period from forming stratum basale to dander is also about two weeks. Therefore the whole keratinization process spends about four weeks to complete. This period is also known as "a big cycle of skin growth". When the stratum corneum has been damaged by extraneous substance or environmental factors, the renewal speed will be accelerated to dislodge the extraneous substance and repair the skin. The stratum corneum is not only the body part to provide basic anti-friction effect, but also the body part to directly contact cosmetics and skin care products.

The upper portion of stratum corneum may be further divided into two layers, including, from top to bottom, a phospholipid layer and a skin bacteria layer. The phospholipid layer is formed by phospholipid. The skin bacteria layer is also called the probiotic layer or normal bacteria layer, which is with a close relation with a balance of skin health. A flora existing in the skin bacteria layer can be divided into a normal flora and a harmful flora, which is harmful to the human body. When the skin is in healthy condition, the proportion of the normal flora in the bacterial flora of the skin bacteria layer should be greater than that of the harmful flora; on the contrary, when the skin is in unhealthy condition, the proportion of harmful bacteria in the bacterial flora of the skin layer is most likely to be greater than that of the normal flora.

The lowermost layer of the epidermis is the stratum basale. A basement membrane is between the stratum basale and the dermis. The basement membrane is located below the stratum basale and serves as a bridge between the epidermis and the dermis. The basement membrane has fibroblasts, which are used to make collagen. In detail, the basement membrane is mainly composed of type IV collagen, which is for maintaining skin nutrients and transferring water in a normal condition. In addition, the basement membrane could also maintain the structure between the epidermis and dermis to keep the skin healthy.

The signs of the deterioration of the skin condition include the occurrence of epidermal desquamation of the skin. The epidermal desquamation means that the stratum corneum is uneven stacked. The uneven stacked stratum corneum is caused by the poor binding force between the cells of the patient's skin, which increases the skin's renewal speed. The continuous cell division of the epidermis leads to the continuous stacking of keratinocytes to cause the stratum corneum uneven stacking. The reasons of inducing the stratum corneum uneven stacking are very complex, which may be caused by the unbalanced structure of the phospholipid layer and the skin bacteria layer due to the detergent, the allergic reaction of the patient's skin, which result in a relatively reduced number of bacterial flora or a significant change in the bacterial flora ratio of the skin bacteria layer. These reasons may cause the stratum corneum uneven stacking. To improve the deterioration of skin conditions, skin repair following physiological pathways of skin structure affected by skin disorders is a very first step to start with.

SUMMARY OF THE INVENTION

Therefore one objective of present invention is to provide a use of *Magnolia figo* extract in the manufacture of a compound for reducing epidermal desquamation and promoting wound healing, wherein the compound can be easily absorbed by the skin and quickly reaches the deep layer of the skin to perform skin repair and/or help wound healing.

In order to overcome the technical problems in prior art, the present invention provides a use of *Magnolia figo* extract in the manufacture of a compound for reducing epidermal desquamation and promoting wound healing.

In one embodiment of the present invention, the use of *Magnolia figo* extract in the manufacture of the compound for reducing epidermal desquamation and promoting wound healing is provided, wherein the *Magnolia figo* extract is *Magnolia figo* essential oil extract of 0.01 to 0.15 wt % or *Magnolia figo* water extract of 90 to 99 wt %.

In one embodiment of the present invention, the use of *Magnolia figo* extract in the manufacture of the compound for reducing epidermal desquamation and promoting wound healing is provided, wherein the *Magnolia figo* extract is *Magnolia figo* essential oil extract of 0.1 wt %.

In one embodiment of the present invention, the use of *Magnolia figo* extract in the manufacture of a compound for reducing epidermal desquamation and promoting wound healing, wherein the *Magnolia figo* extract is *Magnolia figo* water extract of 99 wt %.

In one embodiment of the present invention, the use of *Magnolia figo* extract in the manufacture of the compound for reducing epidermal desquamation and promoting wound healing is provided, wherein the *Magnolia figo* essential oil extract is prepared by the following steps: an extraction step of immersing the *Magnolia figo* extract in an organic solvent to extract a fat-soluble solvent with the components of the *Magnolia figo* extract; a filtering step of filtering the impurities in the fat-soluble solvent to obtain a filtered fat-soluble solvent; a separation step of separating and eliminating the organic solvent in the filtered fat-soluble solvent from the filtered fat-soluble solvent, wherein the filtered fat-soluble solvent from which the organic solvent has been separated and eliminated is a condensed body; a dissolving step of adding alcohol to the condensed body to dissolve the essential oil in the condensed body to obtain an alcohol essential oil; and a distillation step of distilling the alcohol essential oil to get the *Magnolia figo* essential oil extract.

In one embodiment of the present invention, the use of *Magnolia figo* extract in the manufacture of the compound for reducing epidermal desquamation and promoting wound healing is provided, wherein the *Magnolia figo* water extract is prepared by the following steps: a pre-treatment step of washing and breaking the flower of *Magnolia figo*; and an extraction step of obtaining the water extract in a low-temperature vacuum extraction manner.

In one embodiment of the present invention, the use of *Magnolia figo* extract in the manufacture of the compound for reducing epidermal desquamation and promoting wound healing is provided, wherein the *Magnolia figo* extract contains: cadinol, α-cubebene, 2-ethyl-1-hexanol, α-copaene, linalool, β-cubebene, β-elemene, cryophyllene, γ-elemene, 2-methyl-butanoic acid, α-humulene, germacrene D, β-selinene, α-selinene, δ-cadinene, 1-nonadecene, germacrene B, cubebol, caryophyllene epoxide, nerolidol, and Methyl(Z)-5,11,14,17-eicosatetraenoate.

In one embodiment of the present invention, the use of *Magnolia figo* extract in the manufacture of the compound for reducing epidermal desquamation and promoting wound healing is provided, wherein the compound contains a compound carrier selected from a gel or an olive oil.

In one embodiment of the present invention, the use of *Magnolia figo* extract in the manufacture of the compound for reducing epidermal desquamation and promoting wound healing is provided, wherein the compound is applied to skin surface.

By way of the technical means adopted by the present invention, the compound can be easily absorbed by the user's skin, quickly reach the deep layer of the skin, and thus gain the merit of promoting skin repair and/or help wound healing. In addition, while achieving the effect of promoting skin repair and/or helping wound healing, the compound can also improve the user's skin moisture retention, skin color changes and other common skin condition indicators.

DETAILED DESCRIPTION OF THE PREFERRED EMBODIMENTS

The preferred embodiments of the present invention are described in detail below with reference to FIG. 1 to FIG. 9. The description is used for explaining the embodiments of the present invention only, but not for limiting the scope of the claims.

Figure 1A:
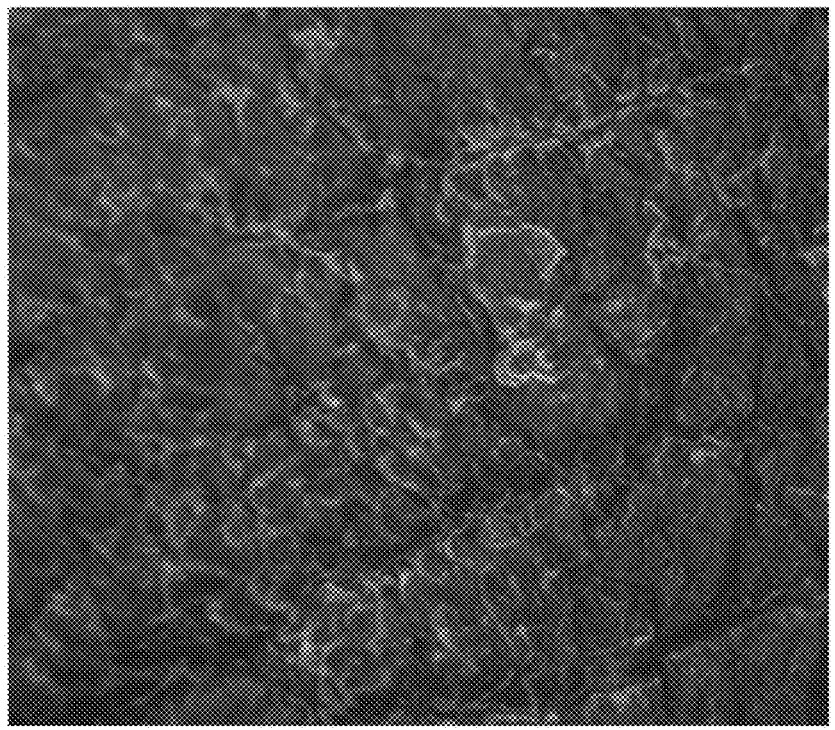
FIG. 1A is a drawing illustrating the skin repair effect of a use of *Magnolia figo* extract in the manufacture of a compound for reducing epidermal desquamation and promoting wound healing according to an embodiment of the present invention.
Figure 1B:
FIG. 1B is a drawing illustrating the skin repair effect of the use of *Magnolia figo* extract in the manufacture of the compound for reducing epidermal desquamation and promoting wound healing according to the embodiment of the present invention.

As shown in FIGS. 1A to 1B, in an embodiment of the present invention, a use of *Magnolia figo* extract in the manufacture of a compound for reducing epidermal desquamation and promoting wound healing is provided, wherein the *Magnolia figo* extract is *Magnolia figo* essential oil extract of 0.01 to 0.15 wt %; the compound includes a compound carrier, the compound carrier is a gel; and the compound is applied to skin surface.

As shown in FIGS. 1A to 1B, the compound containing the *Magnolia figo* essential oil extract of 0.1 wt % and the gel is applied to desquamated skin surface, and the skin desquamation improvement effect of the compound in skin repair is observed according to the changes in the skin surface image. This experiment and other related experiments use the active skin surface analysis system (Visioscan® VC 98) to detect the condition of the skin surface and the results is presented with image and data, in which the image is intended to present skin structure and degree of dryness, the data of this experiment shows the percentage of the skin desquamation improvement effect, and the data of wound healing experiment shows the percentage of the wound healing improvement effect. FIG. 1A shows the skin condition of the subject's skin before the compound is applied, and it can be observed that the subject's skin shows obvious epidermal desquamation. FIG. 1B shows the skin condition after the compound is applied to the skin surface every day for 28 days, and it can be observed that the subject's epidermal desquamation has been significantly improved. The result of Visioscan® VC 98 shows that the subject's skin has a good skin desquamation improvement effect (for example: 81%).

Figure 2A:
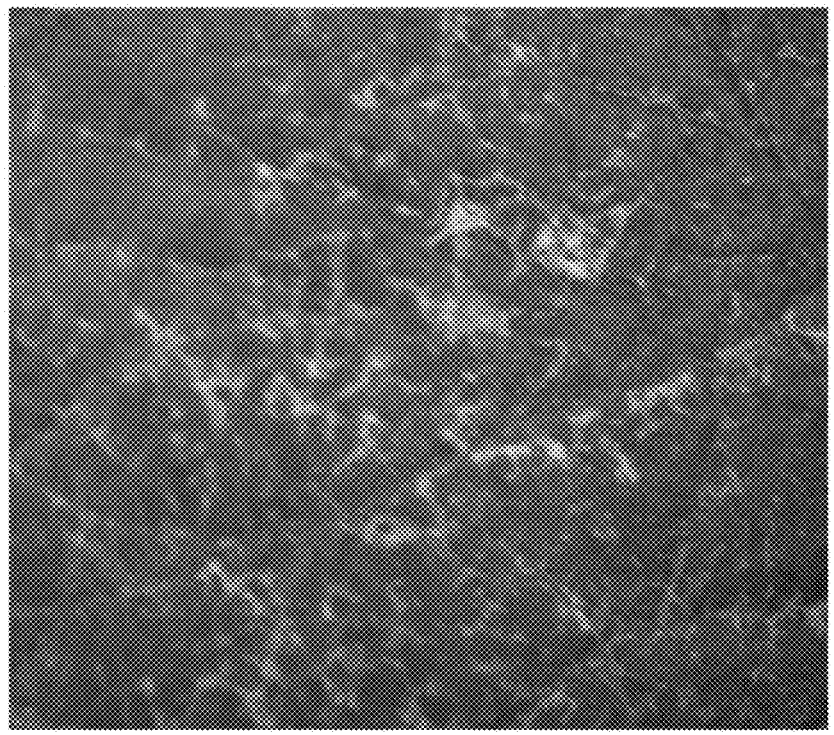
FIG. 2A is a drawing illustrating the skin repair effect of a use of *Magnolia figo* extract in the manufacture of a compound for reducing epidermal desquamation and promoting wound healing according to another embodiment of the present invention.
Figure 2B:
FIG. 2B is a drawing illustrating the skin repair effect of the use of *Magnolia figo* extract in the manufacture of the compound for reducing epidermal desquamation and promoting wound healing according to the embodiment of the present invention.

As shown in FIGS. 2A to 2B, in an embodiment of the present invention, the use of *Magnolia figo* extract in the manufacture of a compound for reducing epidermal desquamation and promoting wound healing is provided, the *Magnolia figo* extract is *Magnolia figo* water extract of 90 to 99 wt %; the compound carrier contained in the compound is a gel; and the compound is applied to skin surface.

As shown in FIGS. 2A to 2B, the compound containing the *Magnolia figo* essential oil extract of 99 wt % and the gel is applied to desquamated skin surface, and the skin desquamation improvement effect of the compound in skin repair is observed according to the changes in the skin surface image. FIG. 2A shows the skin condition of the subject's skin before the compound is applied, and it can be clearly observed, by using Visioscan® VC 98, that the subject's skin shows epidermal desquamation. FIG. 1B shows the skin condition after the compound is applied to the skin surface every day for 28 days, and it can be observed that the subject's epidermal desquamation has been slightly improved. The result of Visioscan® VC 98 shows that the subject's skin has a good skin desquamation improvement effect (for example: 59%).

In detail, as shown in FIGS. 1A to 2B, two experiments were performed in the present invention. The compounds used in the two experiments are respectively a compound containing 0.1 wt % of the *Magnolia figo* essential oil extract and the gel (also referred to as "FMO-01 gel") and a compound containing 99 wt % of the water extract and the gel (also referred to as "FMW-01 gel"). As the result, it can be seen that the FMO-01 gel produces a far greater improvement effect on skin desquamation than the FMW-01 gel according to the percentage of the skin desquamation improvement effect exhibited after the compound has been used for 28 consecutive days. This is because the *Magnolia figo* essential oil extract contained in the FMO-01 gel is a natural liposome (lipid), which is much closer to the phospholipid layer of the skin than some high effect compounds such as hyaluronic acid, natural moisturizing factor, and copper peptide. Furthermore, the molecular weight of the *Magnolia figo* essential oil extract is small (less than 300 Da), so the *Magnolia figo* essential oil extract can be absorbed into the deep layers of the skin through the capillaries of the skin very quickly and easily to promote skin cell repair.

Figure 3A:
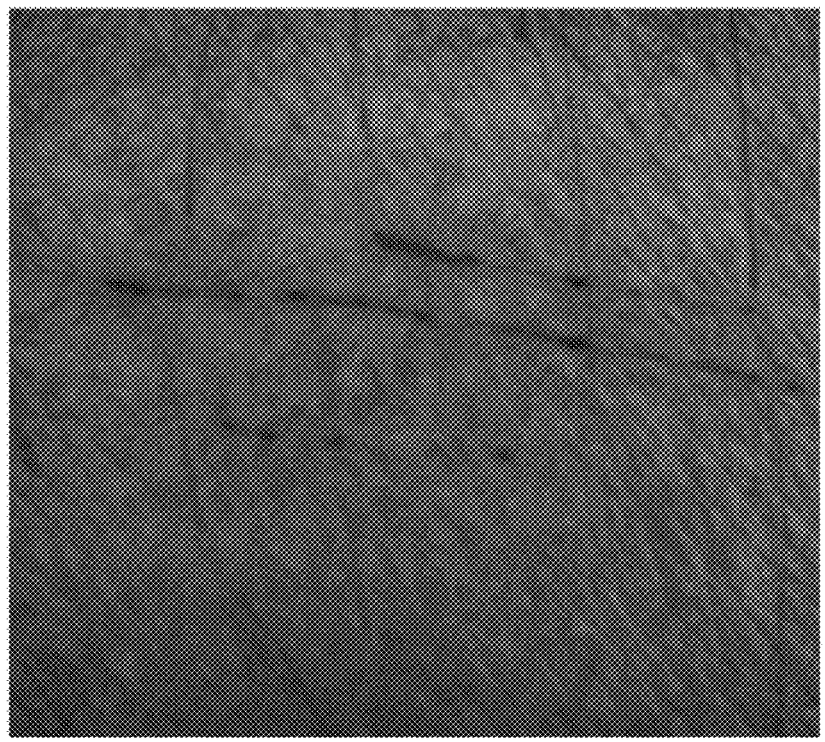
FIG. 3A is a drawing illustrating the skin repair effect of a use of *Magnolia figo* extract in the manufacture of a compound for reducing epidermal desquamation and promoting wound healing according to another embodiment of the present invention.
Figure 3B:
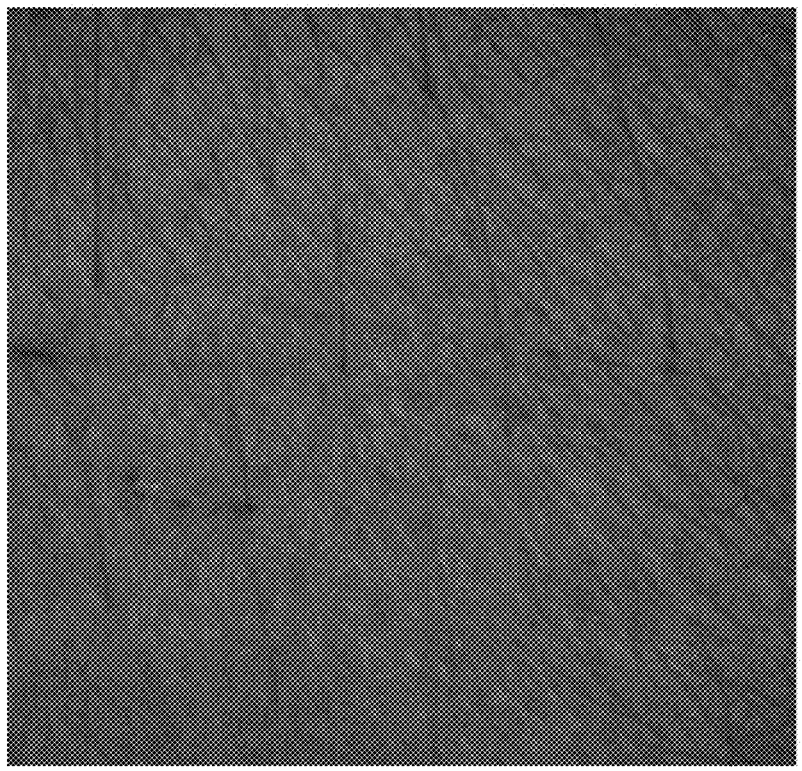
FIG. 3B is a drawing illustrating the skin repair effect of the use of *Magnolia figo* extract in the manufacture of the compound for reducing epidermal desquamation and promoting wound healing according to the embodiment of the present invention.

As shown in FIGS. 3A to 3B, in an embodiment of the present invention, the use of *Magnolia figo* extract in the manufacture of a compound for reducing epidermal desquamation and promoting wound healing is provided, wherein the *Magnolia figo* extract is *Magnolia figo* essential oil extract of 0.01 to 0.15 wt %; the compound contains a compound carrier, the compound carrier is a gel; and the compound is applied to skin surface.

As shown in FIGS. 3A to 3B, the compound containing the *Magnolia figo* essential oil extract of 0.1 wt % and the gel is applied to the surface of the skin scratched by animal, and the improvement effect of the compound on wound healing is observed according to the image changes of the skin surface. FIG. 3A shows the skin condition of the subject's injured skin before the compound is used. The wound on the subject's skin surface can be observed by using the detection of Visioscan® VC 98. FIG. 3B shows the wound on the skin surface to which the compound has been applied for several consecutive days. After 7 days, the wound on the skin becomes less obvious, and the depth of the wound becomes shallower, showing that the subject's wound healing situation has been improved after the compound is applied.

As shown in FIGS. 4A to 4D, in an embodiment of the present invention, the use of *Magnolia figo* extract in the manufacture of a compound for reducing epidermal desquamation and promoting wound healing is provided, wherein the *Magnolia figo* extract is *Magnolia figo* essential oil extract of 0.01 to 0.15 wt %; the compound carrier contained in the compound is a olive oil; and the compound is applied to skin surface.

Figure 4A:
FIG. 4A is a drawing illustrating the skin repair effect of a use of *Magnolia figo* extract in the manufacture of a compound for reducing epidermal desquamation and promoting wound healing according to another embodiment of the present invention.
Figure 4B:
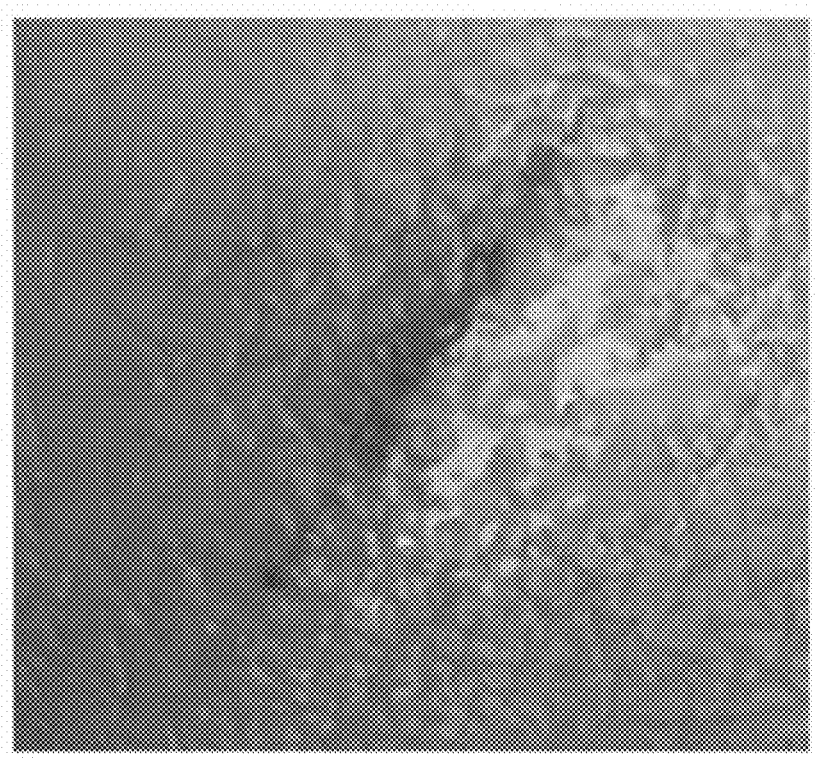
FIG. 4B is a drawing illustrating the skin repair effect of the use of *Magnolia figo* extract in the manufacture of the compound for reducing epidermal desquamation and promoting wound healing according to the embodiment of the present invention.
Figure 4C:
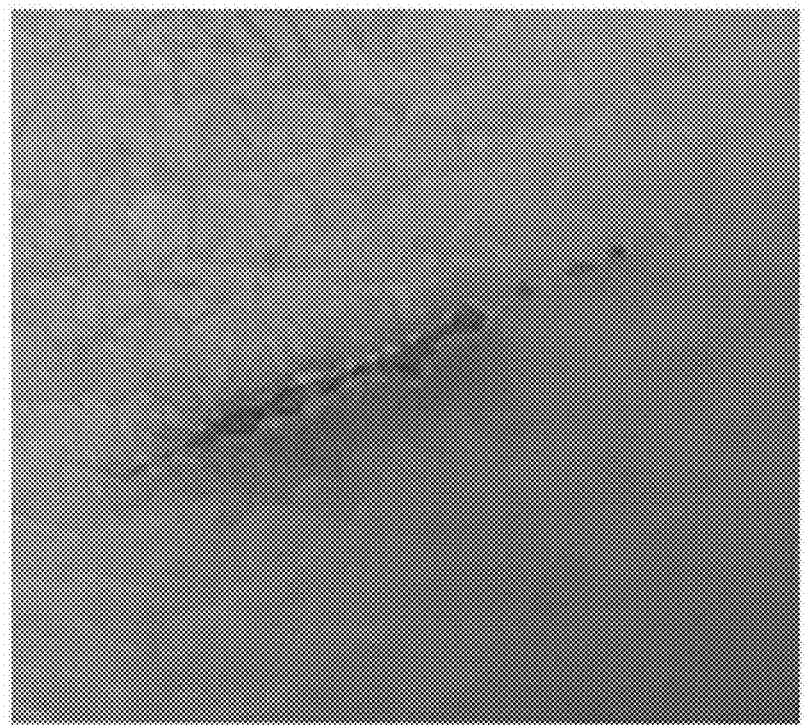
FIG. 4C is a drawing illustrating the skin repair effect of the use of *Magnolia figo* extract in the manufacture of the compound for reducing epidermal desquamation and promoting wound healing according to the embodiment of the present invention.
Figure 4D:
FIG. 4D is a drawing illustrating the skin repair effect of the use of *Magnolia figo* extract in the manufacture of the compound for reducing epidermal desquamation and promoting wound healing according to the embodiment of the present invention.

As shown in FIGS. 4A to 4D, the compound containing 0.1 wt % of the *Magnolia figo* essential oil extract and the olive oil is applied to a cut wound skin surface, and the improvement effect of the compound on wound healing is observed according to the image changes of the skin surface. FIG. 4A shows the skin condition of the subject's skin after injury and before the compound is applied, and the wound on the subject's skin surface can be observed through the detection of the camera. FIG. 4B shows the wound condition of the skin surface to which the compound is applied for 24 hours. FIG. 4C shows the wound condition after 48 hours, the detection result taken by the camera shows that the skin of the subject has a good wound healing improvement effect (for example: 31%). FIG. 4D shows the wound condition on the 7th day, the detection result taken by the camera shows that the subject's skin has a good wound healing improvement effect (for example: 85%), and it can also be found, by visual observation, that the scar area has been reduced. It shows that the subject's wound healing has been significantly improved after the compound is applied.

In detail, as shown in FIGS. 3A to 4D, two experiments were performed in the present invention. The compounds used in the two experiments are respectively a compound containing 0.1 wt % of the essential oil extract and the gel (referred to as "FMO-01 gel") and a compound containing 99 wt % of the water extract and the gel (referred to as "FMO-01 olive oil"). The two experiments are to observe the wound healing improvement effect of the wounds with different severity of skin after the compounds have been respectively applied, wherein the cut wound is more severe than the animal scratch, so in the experiment of the present invention of observing the effect of improving wound healing of cut wounds, as the compound, the FMO-01 olive oil which has a stronger penetrating power than the FMO-01 gel is used, to make the *Magnolia figo* essential oil extract can be absorbed into the deep layer of the skin through the capillaries of the skin very quickly and easily to help the wound healing.

Figure 5:
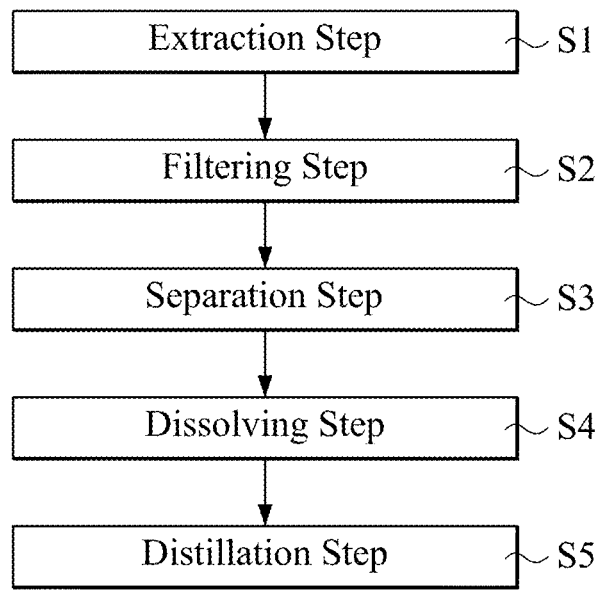
FIG. 5 is a drawing illustrating the flow chart of *Magnolia figo* extraction of the skin repair effect of use of *Magnolia figo* extract in the manufacture of a compound for reducing epidermal desquamation and promoting wound healing according to an embodiment of the present invention.

As shown in FIG. 5, in an embodiment of the present invention, the use of *Magnolia figo* extract in the manufacture of a compound for reducing epidermal desquamation and promoting wound healing is provided, wherein the *Magnolia figo* essential oil extract is prepared by the following steps: an extraction step S1 of immersing the *Magnolia figo* extract in an organic solvent to extract a fat-soluble solvent with the components of the *Magnolia figo* extract; a filtering step S2 of filtering the impurities in the fat-soluble solvent to obtain a filtered fat-soluble solvent; a separation step S3 of separating and eliminating the organic solvent in the filtered fat-soluble solvent from the filtered fat-soluble solvent, wherein the filtered fat-soluble solvent from which the organic solvent has been separated and eliminated is a condensed body; a dissolving step S4 of adding alcohol to the condensed body to dissolve the essential oil in the condensed body to obtain an alcohol essential oil; and a distillation step S5 of distilling the alcohol essential oil to get the *Magnolia figo* essential oil extract.

In detail, in the extraction step S1, distillation, supercritical fluid extraction, or other extraction manners can also be used for extracting the *Magnolia figo* extract.

Figure 6:
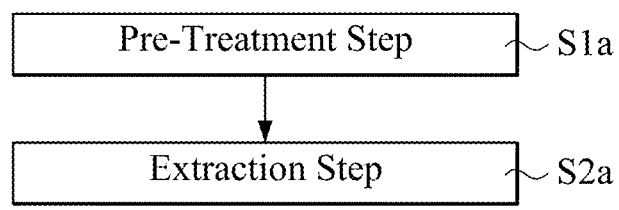
FIG. 6 is a drawing illustrating the flow chart of *Magnolia figo* extraction of the skin repair effect of use of *Magnolia figo* extract in the manufacture of a compound for reducing epidermal desquamation and promoting wound healing according to an embodiment of the present invention.

As shown in FIG. 6, in an embodiment of the present invention, the use of *Magnolia figo* extract in the manufacture of a compound for reducing epidermal desquamation and promoting wound healing is provided, wherein the *Magnolia figo* water extract is prepared by the following steps: a pre-treatment step S1a of washing and breaking the flower of *Magnolia figo*; and an extraction step S2a of obtaining the water extract in a low-temperature vacuum extraction manner.

The compound of the present invention can not only be used to promote skin repair and/or wound healing, but also have obvious effects on enhancing skin moisture retention, preventing moisture evaporating through the skin, whitening skin, improving skin dullness, making skin rosy, and other aspects.

Figure 7:
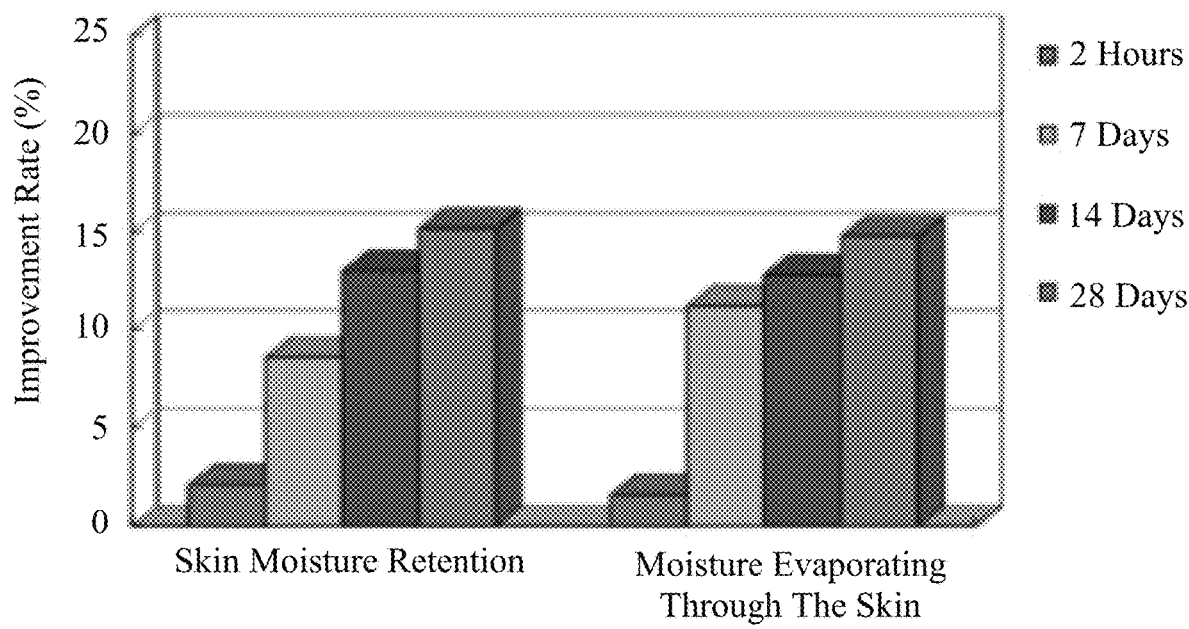
FIG. 7 is a drawing illustrating the schematic diagram of the effect of skin moisture retention changes of the skin repair effect of use of *Magnolia figo* extract in the manufacture of a compound for reducing epidermal desquamation and promoting wound healing according to another embodiment of the present invention.

As shown in FIG. 7, on the 28th day after the compound containing 0.1 wt % of the essential oil extract and the gel (referred to as 0.1% FMO-01 gel) is applied for 28 consecutive days, it can be seen that the 0.1% FMO-01 gel provides an improvement rate of 15.2% for skin moisture retention, and an improvement rate of 14.8% for prevents moisture evaporating through the skin. Table 1 shows the effects of skin whitening, dullness improvement and rosy skin. In terms of skin whitening, on the 28th day after the 0.1% FMO-01 gel is applied for 28 consecutive days, the skin whitening value ($\Delta L$ value>1.50 refers sensible improvement in color difference) increased by 1.65; in terms of improving skin dullness, the $\Delta b$ value of the yellow tone of the skin can be reduced by 1.49 ($\Delta b$ value<−1.50 refers be able to improve the dull skin color difference); in terms of the effect of making the skin rosy, the red tone $\Delta a$ value of the skin can be increased by 0.96.

TABLE 1

| Function | | 0.1% FMO-01 gel | 99% FMW-01 gel | 10% FMW-01 gel |
|---|---|---|---|---|
| Skin whitening value | 2 hours | $\Delta L$: +0.18 | $\Delta L$: +0.14 | $\Delta L$: +0.11 |
|  | 7 days | $\Delta L$: +0.65 | $\Delta L$: +0.55 | $\Delta L$: +0.31 |
|  | 14 days | $\Delta L$: +1.30 | $\Delta L$: +0.77 | $\Delta L$: +0.66 |
|  | 28 days | $\Delta L$: +1.65 | $\Delta L$: +0.97 | $\Delta L$: +0.85 |
| Red tone | 2 hours | $\Delta a$: +0.46 | $\Delta a$: +0.60 | $\Delta a$: −0.26 |
|  | 7 days | $\Delta a$: +1.10 | $\Delta a$: +0.24 | $\Delta a$: −0.22 |
|  | 14 days | $\Delta a$: +0.76 | $\Delta a$: +0.73 | $\Delta a$: +0.09 |
|  | 28 days | $\Delta a$: +0.96 | $\Delta a$: +0.59 | $\Delta a$: −0.16 |
| Yellow tone | 2 hours | $\Delta b$: −0.06 | $\Delta b$: −0.05 | $\Delta b$: +0.05 |
|  | 7 days | $\Delta b$: −0.56 | $\Delta b$: −0.48 | $\Delta b$: −0.58 |
|  | 14 days | $\Delta b$: −1.19 | $\Delta b$: −1.21 | $\Delta b$: −0.44 |
|  | 28 days | $\Delta b$: −1.49 | $\Delta b$: −1.24 | $\Delta b$: −0.49 |

Figure 8:
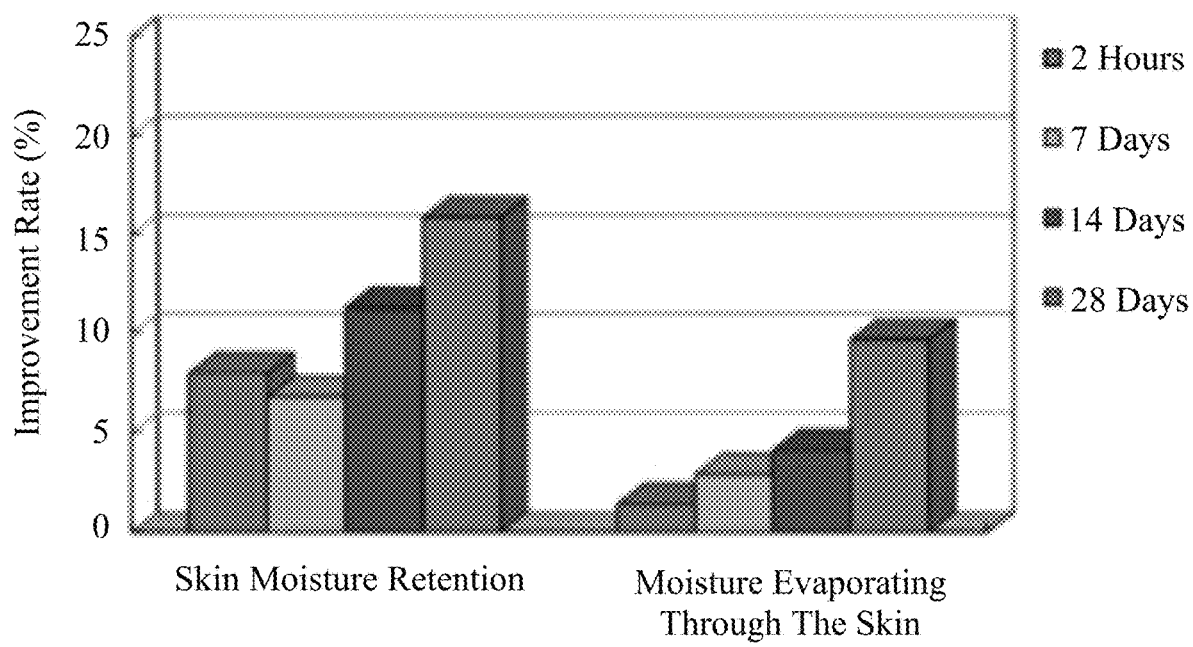
FIG. 8 is a drawing illustrating the schematic diagram of the effect of skin moisture retention changes of the skin repair effect of use of *Magnolia figo* extract in the manufacture of a compound for reducing epidermal desquamation and promoting wound healing according to another embodiment of the present invention.

As shown in FIG. 8, on the 28th day after the compound containing 0.1 wt % of the water extract and the gel (referred to as 99% FMW-01 gel) has been applied for 28 consecutive days, the 99% FMW-01 gel provides an improvement rate of 15.9% for skin moisture retention, and an improvement rate of 9.7% for prevents moisture evaporating through the skin. Table 1 shows the effects of skin whitening, dullness improvement and rosy skin. In terms of skin whitening, on the 28th day after the 99% FMW-01 gel has been applied for 28 consecutive days, the skin whitening value ($\Delta L$ value>1.50 refers sensible improvement in color difference) increased by 0.97; in terms of improving skin dullness, the $\Delta b$ value of the yellow tone of the skin can be reduced by 1.24 ($\Delta b$ value<−1.50 refers be able to improve the dull skin color difference); and in terms of the effect of making the skin rosy, the red tone $\Delta a$ value of the skin can be increased by 0.59.

Figure 9:
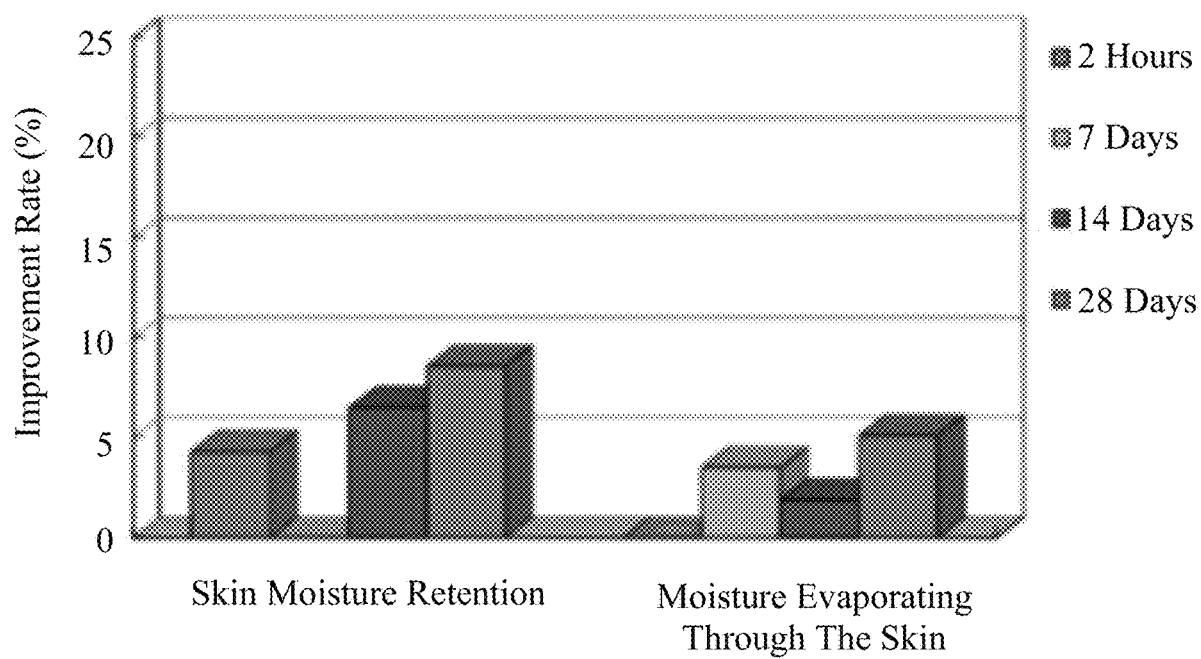
FIG. 9 is a drawing illustrating the schematic diagram of the effect of skin moisture retention changes of the skin repair effect of use of *Magnolia figo* extract in the manufacture of a compound for reducing epidermal desquamation and promoting wound healing according to another embodiment of the present invention.

As shown in FIG. 9, on the 28th day after the compound containing 10 wt % of the water extract and the gel (referred to as 99% FMW-01 gel) has been applied for 28 consecutive days, the 10% FMW-01 gel provides an improvement rate of 8.6% for skin moisture retention, and an improvement rate of 5.1% for prevents moisture evaporating through the skin. Table 1 shows the effects of skin whitening, dullness improvement and rosy skin. In terms of skin whitening, on the 28th day after the 99% FMW-01 gel has been applied for 28 consecutive days, the skin whitening value ($\Delta L$ value>1.50 refers sensible improvement in color difference) increased by 0.85; in terms of improving skin dullness, the $\Delta b$ value of the yellow tone of the skin can be reduced by 0.49 ($\Delta b$ value<−1.50 refers be able to improve the dull skin color difference); and in terms of the effect of making the skin rosy, the red tone $\Delta a$ value of the skin can be increased by 0.16.

In an embodiment of the present invention, a use of *Magnolia figo* extract in the manufacture of a compound for reducing epidermal desquamation and promoting wound healing is provided, wherein the *Magnolia figo* extract contains: cadinol, α-cubebene, 2-ethyl-1-hexanol, α-copaene, linalool, β-cubebene, β-elemene, cryophyllene, γ-elemene, 2-methyl-butanoic acid, α-humulene, germacrene D, β-selinene, α-selinene, δ-cadinene, 1-nonadecene, germacrene B, cubebol, caryophyllene epoxide, nerolidol, and Methyl(Z)-5,11,14,17-eicosatetraenoate.

In detail, the *Magnolia figo* extract contains a variety of phytochemistry constituents that are beneficial to the human body. Among them, cadinol (formula 1) is effective against vector mosquito larvae.

[Formula 1]

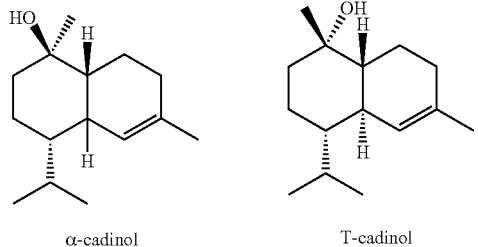

α-cadinol    T-cadinol

In detail, the cubebene (formula 2) contained in the *Magnolia figo* extract has antibacterial and anti-allergic effects.

[Formula 2]

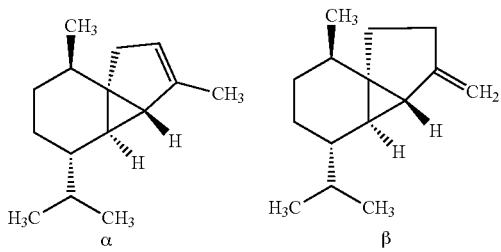

α    β

In detail, the copaene (formula 3) contained in the *Magnolia figo* extract has antioxidant and antibacterial effects.

[Formula 3]

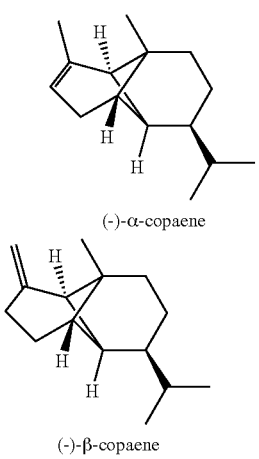

(-)-α-copaene (-)-β-copaene

In detail, the elemene (formula 4) contained in the *Magnolia figo* extract is an anti-cancer and anti-tumor active ingredient.

[Formula 4]

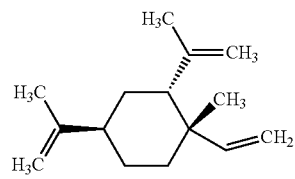

In detail, the caryophyllene (formula 5) contained in the *Magnolia figo* extract has antibacterial and antioxidant effects, and can be used as a fixative or as a natural insecticide.

[Formula 5]

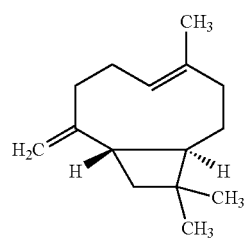

By the technical means adopted by the present invention, the compound with a small molecular weight can be easily absorbed by the skin, to reach the basement membrane quickly, and thereafter to promote the repair of skin disorder, restore the blood vessels around the basement membrane to its proper elasticity, avoid the loss of a large amount of collagen, ensure the continuous proliferation of collagen, rebuild blood vessels and collagen, restore the binding force between epidermal cells and cells to the best state, and improve the uneven stacking of the stratum corneum to reduce the epidermis skin deterioration such as scaling and cracking occurs. The present invention further has the effect of promoting wound healing, and the compound carrier of the compound may be gel or olive oil depending on the severity of the injury. In addition, the present invention also has obvious effects on enhancing skin moisture retention, preventing moisture evaporating through the skin, whitening skin, improving skin dullness, and making skin rosy.

In addition, conventional biomedical materials and skin medical-related products have relatively large molecular weights and can only penetrate at most to the stratum corneum to exhibit temporary effects rather than long-term effects. Compared with conventional biomedical materials and skin medical-related products, the technical means adopted by the present invention can alleviate or solve the skin problems fundamentally at the cellular level, and since the present invention does not involve animals sourced composition, so it raises no morally controversial issue.

The above description should be considered as only the discussion of the preferred embodiments of the present invention. However, a person having ordinary skill in the art may make various modifications without deviating from the present invention. Those modifications still fall within the scope of the present invention.

What is claimed is:

1. A method for reducing epidermal desquamation and promoting wound healing, said method comprising applying a composition containing *Magnolia figo* extract to skin surface of a subject in need thereof wherein the *Magnolia figo* extract contains:

cadinol, α-cubebene, 2-ethyl-1-hexanol, α-copaene, linalool, β-cubebene, β-elemene, cryophyllene, γ-elemene, 2-methyl-butanoic acid, α-humulene, germacrene D, β-selinene, α-selinene, δ-cadinene, 1-nonadecene, germacrene B, cubebol, caryophyllene epoxide, nerolidol, and Methyl(Z)-5,11,14,17-eicosatetraenoate.

2. The method as claimed in claim 1, wherein the *Magnolia figo* extract is *Magnolia figo* essential oil extract of 0.01 to 0.15 wt %.

3. The method as claimed in claim 2, wherein the *Magnolia figo* extract is *Magnolia figo* essential oil extract of 0.1 wt %.

4. The method as claimed in claim 1, wherein the composition contains a carrier selected from a gel or an olive oil.

5. The method as claimed in claim 2, wherein the composition contains a carrier selected from a gel or an olive oil.

* * * * *